United States Patent [19]
Yardley

[11] 3,987,105

[45] Oct. 19, 1976

[54] PROCESS FOR METHOXYMETHYLATION OF PHENOLIC HYDROXYL GROUPS

[75] Inventor: John P. Yardley, King of Prussia, Pa.

[73] Assignee: American Home Products Corporation, New York, N.Y.

[22] Filed: Apr. 25, 1975

[21] Appl. No.: 571,470

[52] U.S. Cl. .................... 260/600 R; 260/613 D; 260/592; 260/562 A
[51] Int. Cl.² .................. C07C 41/00; C07C 45/00
[58] Field of Search ............. 260/613 D, 600, 592, 260/562 A, 600 R

[56] References Cited
UNITED STATES PATENTS

| | | | |
|---|---|---|---|
| 2,463,541 | 3/1949 | Houk | 260/613 D |
| 2,833,829 | 5/1958 | Schrader | 260/613 D |
| 3,127,450 | 3/1964 | Lorette et al. | 260/615 A X |

*Primary Examiner*—Bernard Helfin
*Attorney, Agent, or Firm*—Robert Wiser

[57] ABSTRACT

A process for preparing methoxymethyl ethers of phenols utilizing dimethoxy methane is described. The thus-protected phenols are useful as intermediates in a variety of reaction sequences.

4 Claims, No Drawings

PROCESS FOR METHOXYMETHYLATION OF PHENOLIC HYDROXYL GROUPS

BACKGROUND OF THE INVENTION

Preparing the methoxymethyl ether of a phenol is a well-known method for protecting phenolic hydroxyl groups from unwanted reactions [see, for example, L. F. Fieser and M. Fieser, Reagents for Organic Synthesis, p. 133, John Wiley and Sons, Inc., New York, New York, 1967; J. F. W. McOmie, Advances in Organic Chemistry, 3, 232 (1963)]. The reagent most often utilized in the prior art to effect this transformation has been chloromethyl methyl ether. However, since this substance has recently been indicated as possessing a carcinogenic potential [Federal Register, 39, 3757 (1974)], its use as a reagent has become less desirable. The only remaining, art-recognized, reagent which is utilized in a one-step preparation of methoxymethyl ethers is methoxymethyl methanesulfonate (U.S. Pat. No. 3,737,449). This substance has been described as a corrosive and extremely hygroscopic liquid, thus necessitating special techniques for its use and manipulation, which techniques may often be inconvenient and time-consuming.

The instant invention advantageously provides an alternative procedure for the conversion of phenols to their methoxymethyl ether derivatives. This procedure has the additional advantage of utilizing for this conversion, the readily available, unobjectionable reagent, dimethoxymethane.

The phenol methoxymethyl ethers, preparable by the instant process, are useful as reaction intermediates when it is desired to protect the phenol function from an unwanted reaction and subsequently regenerate the phenol [see, for example, Belgian Patent 797,827; R. L. Edwards and I. Mir, J. Chem Soc. (c), 411 (1967); M. A. Abdel-Rahman, H. W. Elliot, R. Binks, W. Kunig, and H. Rapoport, J. Med. Chem., 9, 1 (1965)]. Of particular interest and importance is the protected phenol, m-methoxymethoxybenzaldehyde, an intermediate used in the synthesis of several potent analgesic compounds (Belgian Patent 797,827); one such compound is 1-cis-2-(α-dimethylamino-m-hydroxybenzyl)-cyclohexanol.

SUMMARY OF THE INVENTION

The invention sought to be patented in a principal process aspect resides in the concept of a process for preparing a compound of the structure:

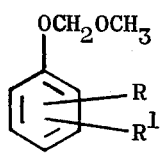

wherein R and R$^1$ may be the same or different and are chosen from the group consisting of hydrogen, alkyl of from 1 to 6 carbon atoms, alkoxy of from 1 to 6 carbon atoms, m-halo, p-halo, m-nitro, p-nitro, m-acylamino of from 1 to 6 carbon atoms, p-acylamino of from 1 to 6 carbon atoms, m-acyl of from 1 to 6 carbon atoms, and p-acyl of from 1 to 6 carbon atoms; which comprises treating a compound of the structure:

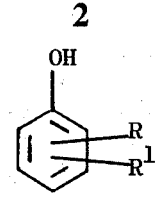

wherein R and R$^1$ are as defined above, with dimethoxymethane and an acid catalyst in the presence of type 3A or 4A molecular sieves.

The invention sought to be patented in a subgeneric process aspect resides in the concept of a process for preparing a compound of the structure:

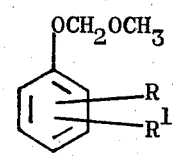

wherein R and R$^1$ may be the same or different and are chosen from the group consisting of hydrogen, alkyl of from 1 to 6 carbon atoms, alkoxy of from 1 to 6 carbon atoms, m-halo, p-halo, m-nitro, p-nitro, m-acylamino of from 1 to 6 carbon atoms p-acylamino of from 1 to 6 carbon atoms, m-acyl of from 1 to 6 carbon atoms, and p-acyl of from 1 to 6 carbon atoms; which comprises treating a compound of the structure:

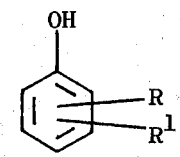

wherein R and R$^1$ are as defined above, with dimethoxymethane and a sulfonic acid catalyst utilizing chloroform or methylene chloride as solvent in the presence of type 3A or 4A molecular sieves.

DESCRIPTION OF THE INVENTION

In carrying out the process of the instant invention, the phenol starting material is reacted with dimethoxymethane in the presence of an acid catalyst. For efficiency of reaction, molecular sieves of type 3A or 4A are conveniently utilized for removal of the reaction-produced methanol and thus drive the reaction toward completion. Molecular sieves and their use will be familiar to those skilled in the art, and are described in L. F. Fieser and M. Fieser, Reagents for Organic Synthesis, p. 703, John Wiley and Sons, Inc., New York, New York, 1967.

Those skilled in the art will also recognize that a particularly efficient manner in which to utilize molecular sieves for the instant process is to contain them in a Soxhlet type extractor and continuously reflux the reaction mixture through them. This procedure is, of course, not critical to the invention and various other methods for using molecular sieves are available and will suggest themselves to those skilled in the art.

In a preferred embodiment of the invention, m-hydroxybenzaldehyde and dimethoxymethane are dissolved in methylene chloride and p-toluenesulfonic acid monohydrate is added. The mixture is refluxed overnight using a Soxhlet extractor containing type 3A molecular sieves, and the product, m-methoxymethoxybenzaldehyde, is isolated and purified by standard procedures. For example, after the reaction mixture cools, triethylamine is added to neutralize the acid catalyst and the mixture is washed with dilute sodium hydroxide solution and water, dried over sodium sulfate and evaporated. The residue is purified by distillation.

By acid catalyst is meant any of the acids known in the art of Organic Chemistry to be useful in catalyzing acetal exchange type reactions; among this group of acids are, for example, p-toluenesulfonic acid, methanesulfonic acid, sulfuric acid, and the like. Neither the reaction solvent, nor the particular acid catalyst utilized are critical aspects of the invention. Other solvents such as chloroform may be used. Similarly any of the acid catalysts may be utilized.

While nucleophilic acids such as hydrogen chloride may be used as catalyst, their use preferably should be avoided since due to their nucleophilicity, competing side reactions would be expected to detrimentally affect the yield of desired product. The use of hydrogen chloride should also be avoided because of the possible in situ production of chloromethyl methyl ether.

It has been observed that the use of methylene chloride as solvent very efficiently removes the reaction-produced methanol with which it forms an azeotrope boiling at 37.8° C. However, as previously discussed, the choice of other solvents, for example to solubilize difficulty soluble reactants, is within the skill of the art and is not considered a critical aspect of the invention.

The reacting phenol may contain a variety of substituents; however, it has been observed that substituents capable of hydrogen bonding the phenolic proton (e.g. nitro, or those containing a carbonyl group), when situated in the ortho position may prevent the reaction from occurring. Thus, o-hydroxyacetophenone has not been observed to react when subjected to the conditions of the instant process and 2,2′-dihydroxybenzophenone yields only a mono methoxy-methylated derivative.

In addition, di-phenols have been observed to react under the conditions of the instant process; thus protocatechualdehyde yields its dimethoxymethylated derivative.

For purposes of the instant invention, the term "acyl" will be understood to mean a substituent of the structure

wherein A may be hydrogen or alkyl of from 1 to 5 carbon atoms. Those skilled in the art will recognize that when A is hydrogen, the acyl group is derived from formic acid and is commonly referred to as the aldehyde function —CHO. Thus, for example, among the various protected phenols contemplated by the instant invention is m-methoxymethoxybenzaldehyde, which is derived from m-hydroxybenzaldehyde.

The following non-limiting examples further illustrate the best mode contemplated by the inventor for carrying out the process of the invention.

EXAMPLE 1 m-Methoxymethoxybenzaldehyde m-Hydroxybenzaldehyde (32 g., 0.25 moles) methylene chloride (500 ml.), dimethoxymethane (100 ml., 1.13 moles), and p-toluenesulfonic acid monohydrate (250 mg.) were refluxed overnight under nitrogen using a Soxhlet extractor containing type 3A molecular sieves (150 g.). The reaction mixture was allowed to cool treated with triethylamine (2 ml.) to neutralize the acid catalyst and washed with 1N NaOH (2 × 200 ml.), water and dried ($Na_2SO_4$). Evaporation of solvent afforded a 28 g. residue, which after distillation, b.p. 92°–105° at 0.7 – 0.8 mm. gave 24.6 g. of m-methoxymethoxybenzaldehyde, (60% yield).

EXAMPLE 2 p-Methoxymethoxybenzaldehyde p-Hydroxybenzaldehyde (91 g.), methylene chloride (1500 ml.), dimethoxymethane (300 ml.), and p-toluenesulphonic acid monohydrate (1 g.) were refluxed 48 hours under nitrogen using a Soxhlet extractor containing a type 3A molecular sieve (325 g.). The reaction mixture was allowed to cool, was washed with 1N NaOH, water and dried ($Na_2SO_4$). Evaporation of solvent and distillation of the residue afforded 83.5 g. p-methoxymethoxybenzaldehyde b.p. 105° at 0.3 mm.

EXAMPLE 3

Methoxymethoxybenzene

Phenol (25 g.) methylene chloride (600 ml.), dimethoxymethane (100 ml.) and p-toluenesulfonic acid monohydrate (0.2 g.) were refluxed for 48 hours under nitrogen using a Soxhlet extractor containing type 3A molecular sieves (150 g.). The reaction mixture was allowed to cool, was washed with 1N NaOH, water, and dried ($Na_2SO_4$). Evaporation of the solvent and distillation of the residue yielded 29.5 g. (80% methoxymethoxybenzene PMR in $CDCl_3$ δ 3.39 [3H singlet, $OCH_3$], δ 5.09 [2H singlet, $OCH_2O$], δ 6.7 – 7.4 [5H multiplet, aromatic protons].

The subject matter which the applicant regards as his is particularly pointed and distintly claimed as follows:

1. A process for preparing a compound of the structure:

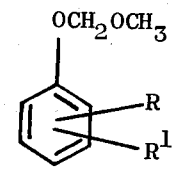

wherein R and $R^1$ may be the same or different and are chosen from the group consisting of hydrogen, alkyl of from 1 to 6 carbon atoms, alkoxy of from 1 to 6 carbon atoms, m-halo, p-halo, m-nitro, p-nitro m-acylamino, p-acylamino, m-acyl and p-acyl wherein the term acyl is a substituent of the structure

wherein A is hydrogen or alkyl of 1 to 5 carbon atoms; which comprises refluxing a compound of the structure:

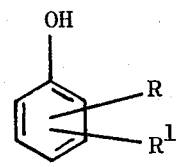

wherein R and R¹ are as defined above, with dimethoxymethane and an acid catalyst in the presence of type 3A or 4A molecular sieves.

2. The process of claim 1 wherein R is hydrogen and R¹ is m-formyl.

3. The process of claim 1 wherein a sulfonic acid is utilized as catalyst and either chloroform, or methylene chloride is utilized as solvent.

4. The process of claim 3 wherein R is hydrogen and R¹ is m-formyl.

* * * * *